United States Patent [19]

Hung et al.

[11] Patent Number: 5,637,748
[45] Date of Patent: Jun. 10, 1997

[54] PROCESS FOR SYNTHESIZING FLUORINATED NITRILE COMPOUNDS

[75] Inventors: Ming-Hong Hung, Wilmington, Del.; Vinayakam Subramanyam, Boothwyn, Pa.

[73] Assignee: E. I. Du Pont de Nemours and Company, Wilmington, Del.

[21] Appl. No.: 396,997

[22] Filed: Mar. 1, 1995

[51] Int. Cl.$^6$ ................................................. C07C 253/20
[52] U.S. Cl. ........................... 558/312; 558/313; 564/135; 564/136
[58] Field of Search ................................. 564/135, 136; 558/312, 313

[56] References Cited

U.S. PATENT DOCUMENTS

| | | | |
|---|---|---|---|
| 3,546,186 | 12/1970 | Gladding et al. | 260/80.73 |
| 4,138,426 | 2/1979 | England | 560/183 |
| 4,281,092 | 7/1981 | Breazeale | 526/247 |

*Primary Examiner*—Johann Richter
*Assistant Examiner*—John Peabody

[57] ABSTRACT

Syntheses of fluorinated amide and fluorinated nitrile compounds are improved by use of particular media for the reactions. Fluorinated amide can also be synthesized in high yield in a neat reaction.

15 Claims, No Drawings

PROCESS FOR SYNTHESIZING FLUORINATED NITRILE COMPOUNDS

FIELD OF THE INVENTION

This invention is in the field of processes for synthesizing nitrile compounds having olefinic functionality. Such nitrile compounds can be used as cure site monomers in fluoroelastomers.

BACKGROUND OF THE INVENTION

Compounds of the general formula $CF_2=CF-R_f-CN$ wherein $R_f$ is perfluoroalkyl or perfluoroalkoxy containing 2–20 carbon atoms are useful as cure site monomers in fluoroelastomers. See, for example, U.S. Pat. No. 3,546,186 (Gladding & Sullivan) or U.S. Pat. No. 4,281,092 (Breazeale). A traditional method for making such compounds is by (a) first reacting the corresponding ester starting material (or a derivative thereof) with ammonia gas at low cooling temperature to form an amide compound, and (b) then converting the amide to the desired nitrile through a dehydration process.

The traditional synthetic approach suffers from low yield due to the problems of a non-homogeneous reaction medium and from difficulties in product separation. Since the solubilities of fluorinated compounds are usually quite low in common organic solvents, a fluorinated solvent such as 1,1,2-trichloro-1,2,2-trifluoroethane (CFC-113) is often used in these reactions as a product extraction solvent. CFCs are now undesirable for environmental reasons, and their manufacture is being phased out. Formation of significant quantities of side-products due to sensitivity of olefin functionality toward the reaction reagents also occurs. See U.S. Pat. No. 4,138,426 (England). The yield from the first step of England Example 8, conducted in ether (ethyl ether), was only 9%, and CFC-113 was employed in separating the reaction product from the reaction mass. In the second step of England, the first step amide was dehydrated to the nitrile in tetrahydrofuran solvent using pyridine and trifluoroacetic anhydride as dehydrating agent. Again, CFC-113 was used to aid separation of the product from the reaction mass.

An improved method of synthesizing these compounds is desired.

SUMMARY OF THE INVENTION

This invention provides an improved process for synthesizing fluoro-nitrile compound of the formula $CF_2=CF-R_f-CN$ from fluoro-ester $CF_2=CF-R_f-COOR$ wherein R is alkyl containing 1–6 carbon atoms, by first reacting the ester with ammonia gas or aqueous ammonium hydroxide, said reaction being carried out either in the absence of solvent, in an oxygen-free solvent, or in a solvent containing oxygen only as ether oxygen bonded to a perfluoroalkyl group, to form fluoro-amide of the formula $CF_2=CF-R_f-CONH_2$, and subsequently reacting said amide with dehydrating agent in anhydrous polar solvent having the formula $R-(CO)-NR'R''$, wherein R is H or alkyl having 1–6 carbon atoms, and R' and R'' are independently alkyl having 1–6 carbon atoms, to form said fluro-nitrile to form said nitrile compound, $R_f$ throughout being perfluoroalkyl or perfluoroalkoxy containing 2–20 carbon atoms. The steps of reacting the fluoro-ester and of reacting the fluoro-amide are also separate aspects of the invention. A preferred solvent for reaction of fluoro-ester is methylene chloride. Preferred solvents for reaction of fluoro-amide include N,N-dimethylformamide and N,N-dimethylacetamide.

DETAILED DESCRIPTION OF THE INVENTION

It has been discovered that yield in the reaction of fluoro-ester with ammonia, or with ammonium hydroxide, to form fluoro-amide can be greatly improved if the reaction is carried out in the absence of solvent, or in oxygen-free solvent, or in solvent containing ether oxygen bonded to a perfluoroalkyl group. Furthermore, when the reaction is so carried out, it is not necessary to use perhalogenated solvent to extract the fluoro-amide from the reaction medium. Additionally, it has been discovered that the reaction of fluoro-amide with pyridine and trifluoroacetic anhydride to form fluoro-nitrile results in solvent and fluoro-nitrile product phases that can be easily separated without the aid of halogenated solvent if the reaction is carried out in polar solvent having a carbonyl group.

Fluoro-ester starting compounds for the process of this invention can have the formula $CF_2=CF-R_f-COOR$, wherein R is alkyl having 1–6 carbon atoms, and $R_f$ is perfluoroalkyl or perfluoroalkoxy having 2–20 carbon atoms. Preferably, R is methyl or ethyl. Preferred $R_f$ is perfluoroalkoxy, including $-[OCF_2CF(CF_3)]_nOCF_2CF_2-$ wherein n=1–5, most preferably n=1, and $-O(CF_2)_k-$ wherein k=2–20, most preferably k=2–4. When $R_f$ is $-(CF_2)_m-$, m=2–12. Preferably, m=2–8. Such fluoro-ester compounds, or precursor acids that are readily esterified, are known. See, for example, U.S. Pat. Nos. 3,546,186; 4,138,486; 4,275,226; and 4,281,092; and Zh. Org. Kim. 16, 540 (1980).

In one aspect of the invention, the reaction of fluoro-ester with ammonia or aqueous ammonium hydroxide to form fluoro-amide of the formula $CF_2=CF-R_f-CONH_2$, wherein $R_f$ is as defined above, is carried out neat, i.e., in the absence of solvent, or in oxygen-free solvent, or in solvent containing only ether oxygen bonded to a perfluoroalkyl group. Preferably, the reaction is carried out in the absence of solvent or in oxygen-free solvent. By "oxygen-free", it is meant that the nominal chemical formula for the solvent contains no oxygen. Preferred solvents for this aspect of the invention are saturated halogenated compounds that are not chlorofluorocarbon (CFC), i.e., are hydrogen-containing halocarbons. Desirably, such solvents have boiling points no higher than 100° C. Methylene chloride is an especially preferred solvent.

The ratio of equivalents of ammonia, or ammonium hydroxide, to fluoro-ester can be in the range 1.0 to 2.5, preferably 1.1 to 2.0.

The reaction of fluoro-ester with ammonia can be carried out at such temperatures as from –80° to 0° C., preferably at –60° to –5° C., most preferably at –20° to –5° C. For reaction of fluoro-ester with aqueous ammonium hydroxide, the reaction can be carried out at such temperatures as from –20° to +25° C., preferably –5° to +20° C., most preferably +10° to +15° C.

When reaction with fluoro-ester is carried out by the process of this invention, desired fluoro-amide is easily separated from the reaction mass, and can be obtained in very pure form by distillation. Molar yields to fluoro-amide from fluoro-ester are high, more than 70%, and usually more than 80%.

In another aspect of the invention, the reaction of fluoro-amide with dehydrating agent to form fluoro-nitrile of the formula $CF_2=CF-R_f-CN$, wherein $R_f$ is as defined above, is carried out in anhydrous polar solvent. Preferred solvents include those having the formula $R-(CO)-NR'R''$, wherein R is H or alkyl having 1–6 carbon atoms, and R' and R" are independently alkyl having 1–6 carbon atoms. Preferably, R is H or methyl, and R' and R" are both methyl or ethyl. Alternatively, R and either R' or R" can be connected to form a cyclic structure. Preferred solvents include N,N-dimethylformamide, N,N-dimethylacetamide, and N-methylpyrrolidone. A preferred dehydrating agent is the combination of pyridine and trifluoroacetic anhydride.

In carrying out the reaction with fluoro-amide in anhydrous polar solvent, the ratio in equivalents of dehydrating reactant to fluoro-amide is usually in the range 1.0–2.5. When the dehydrating agent is pyridine and trifluoroacetic anhydride, the ratio can be in the range 1.0 to 2.0, preferably 1.1 to 1.5 for trifluoroacetic anhydride, and 1.0 to 2.5, preferably 1.0 to 2.0, and most preferably 1.1 to 1.5 for pyridine.

The reaction of fluoro-amide with dehydrating agent can be carried out at temperatures such as from −25° to +25° C., preferably from −15° to 0° C.

When reaction with fluoro-amide is carried out by the process of this invention, desired fluoro-nitrile predominantly separates from the reaction mass as a distinct liquid layer, with the other layer being solvent containing dehydrating agent reaction residues. Fluoro-nitrile can then be obtained in high yield by separating and washing that phase with water, followed by distillation. Molar yields to fluoro-nitrile from fluoro-amide are high, usually more than 75%, and often more than 80%.

The reaction of fluoro-ester with ammonia or ammonium hydroxide to form fluoro-amide and the reaction of fluoro-amide with dehydrating agent in polar solvent to form fluoro-nitrile, together, are a process for synthesizing fluoro-nitrile from fluoro-ester. This sequence can be carried out with isolation and purification of intermediate fluoro-amide. In another embodiment of this invention, the sequence can be carried out consecutively without purifying the intermediate fluoro-amide. In the latter sequence, for example, fluoro-ester can be reacted with anhydrous ammonia gas, preferably in the absence of solvent, followed by removal of excess ammonia and side product methanol under reduced pressure, but without costly and time consuming distillation of the crude fluoro-amide. Crude fluoro-amide can then be dissolved in the polar solvent and reacted with dehydrating agent to form fluoro-nitrile, which can be separated, washed, and purified by distillation as described above. This sequence has the significant advantage of eliminating a purification step.

EXAMPLES

The following code is used in the examples below:
EVE=Methyl perfluoro-(5-methyl-4,7-dioxa-8-nonenoate) [$CF_2$=$CFOCF_2CF(CF_3)OCF_2CF_2$—$COOCH_3$]
AVE=Perfluoro-(5-methyl-4,7-dioxa-8-nonenoyl)amide [$CF_2$=$CFOCF_2CF(CF_3)OCF_2CF_2$—$CONH_2$]
8-CNVE=Perfluoro-(8-cyano-5-methyl-3,6-dioxa-1-octene) [$CF_2$=$CFOCF_2CF(CF_3)OCF_2CF_2$—$CN$]

EXAMPLE 1

Synthesis of AVE from EVE

EVE (84.4 g, 0.2 mol) was dissolved in 240 mL of methylene chloride and cooled to −78° C. Ammonia gas (5 g, 0.29 mol) was then passed into the reaction solution through a gas inlet tube with vigorous stirring while the reaction temperature was controlled below −60° C. After the addition of ammonia was complete, the reaction mixture was stirred at −78° to −60° C. for 2 hr, then warmed to ambient temperature. The $CH_2Cl_2$ solvent was removed by evaporation under vacuum, and then the residue was distilled at reduced pressure. AVE, confirmed by comparison of $^{19}F$ NMR, proton NMR, and GC measurements with those for a reference sample, was recovered as 68 g of a clear, colorless liquid having a boiling point of 80° C. at 1 mmHg or 94°–96° C. at 3 mmHg. Yield to AVE from EVE was 83.5% (molar basis).

CONTROLS A–C

Eperiments A–C were carried out in the way described in Example 1, except that the solvent used in the reaction was tetrahydrofuran (THF) or a mixture of THF and $CH_2Cl_2$. The results summarized in Table 1, including the results of Example 1, indicated that yield of fluoro-amide decreased as the proportion of oxygen-containing solvent increased, and that yield was highest when oxygen-free solvent was used.

TABLE 1

| Solvent Mixtures and Yields of AVE | | | | |
|---|---|---|---|---|
| | Ex. 1 | Ex. 2 | Ex. 3 | Ex. 4 |
| $CH_2Cl_2$(mL) | 240 | 120 | 80 | 0 |
| THF (mL) | 0 | 120 | 160 | 240 |
| Yield | 84 | 74 | 61 | 48 |

EXAMPLES 2–3 AND CONTROL D

Synthesis of AVE from EVE

Examples 2–3 were carried out in the way described in Example 1, except that different oxygen-free solvents were used instead of $CH_2Cl_2$. A different oxygen-containing solvent was used in Control D. The solvents are identified in Table 2. Results also presented in Table 2 show that oxygen-free solvent gave much higher yield to fluoro-amide than solvent containing oxygen as hydroxyl.

TABLE 2

| Yields for Examples 2–3 and Control D | | |
|---|---|---|
| Ex. | Solvent | Yield (%) |
| 2 | $CF_3CHCl_2$ | 74 |
| 3 | $CH_3CFCl_2$ | 84 |
| D | $CF_3CH_2OH$ | 4 |

EXAMPLE 4

Synthesis of AVE from EVE

A glass flask was charged with a mixture of 150 mL of α-hydro-perfluoro(ethyl propyl ether), i.e., $CF3CF2CF2$—O—CFH—CF3, and 27 mL of 28% aqueous ammonium hydroxide (0.4 mol). The flask was cooled in ice water to about 10°–15° C. EVE (84.4 g, 0.2 mol) was added slowly with stirring while the reaction temperature was controlled below 15° C. After additon of EVE was complete, the reaction mixture was warmed to ambient temperature. The bottom organic layer was separated and distilled to obtain 66 g of AVE (81% yield) as a clear, colorless liquid having a boiling point of 94°–96° C. at 3–4 mmHg. This illustrates that a solvent containing an ether oxygen adjacent (bonded) to a perfluoroalkyl group can be used in the process of this invention for synthesis of fluoro-amides from fluoro-esters.

EXAMPLE 5

Synthesis of AVE from EVE

A glass flask was charged with a mixture of 150 mL of methylene chloride and 27 mL of 28% aqueous ammonium hydroxide (0.4 mol). The flask was cooled in ice water to about 10°–15° C. EVE (84.4 g, 0.2 mol) was added slowly with stirring while the reaction temperature was controlled at about 15° C. After additon of EVE was complete, the reaction mixture was warmed to ambient temperature in 1–2 hr. The flask then contained a three-layered liquid. Gas chromatographic (GC) analysis of the top layer, present only in small amount, indicated it to be aqueous residue which was separated and discarded. The middle and bottom layers, which were both mixtures of AVE and CH2Cl2, were combined and distilled to obtain 67 g of AVE as a clear, colorless liquid having a boiling point of 80° C. at 1 mmHg or 94°–96° C. at 3 mmHg. Yield to AVE from EVE was 82.3%.

EXAMPLE 6

Synthesis of AVE from EVE

This example illustrates synthesis of AVE in the absence of solvent. A glass flask cooled at −15° C. was charged with 84.4 g (0.2 mol) of EVE, and then ammonia gas (7 g, 0.412 mol) was bubbled through the EVE liquid. The reaction temperature was controlled at around −15° C. After the addition of ammonia was complete, the mixture was warmed quickly to about 0° C., and residual ammonia and the methanol formed during the reaction were removed by vacuum. The remaining material was then distilled to obtain 69 g of AVE (84.8% yield). The purity of the recovered AVE was greater than 99% as determined by GC.

EXAMPLE 7

Synthesis of 8-CNVE from EVE

AVE (40.7 g, 0.1 mol) was dissolved in 42.5 mL of anhydrous N,N-dimethylformamide (DMF) and cooled to −20° C. Pyridine (9.48 g, 0.12 mol) was added slowly, followed by 25.2 g (0.12 mol) of trifluoroacetic anhydride. The reaction was slightly exothermic and the pot was kept at −10° to −15° C. by external cooling. After addition of trifluoroacetic anhydride was complete, the reaction mixture was warmed to ambient temperature. At this time, a two-layer product mixture was observed. The top layer was mainly DMF solvent, while the bottom layer was essentially the fluoro-nitrile product with very small amount of DMF. The bottom layer was separated, washed with water, and distilled to obtain 33.5 g of the desired 8-CNVE, confirmed by comparison of $^{19}$F NMR, GC, and infrared measurements with those for a reference sample, as a clear, colorless liquid having a boiling point of 102°–104° C. Yield was 86%.

CONTROL E

Experiments were carried out in the same way as Example 7 except that THF was used as the solvent instead of DMF. The reaction solutions developed a yellow color, and more side products were detected by GC analysis. Yields to isolated 8-CNVE product were in the range of 40–50% at best.

CONTROL F

This experiment was carried out in the same way as Example 7 except that methylene chloride was use as the solvent instead of DMF. The yield was reasonable as judged from GC analysis. However, the 8-CNVE product could not be recovered in pure form since 8-CNVE forms a distillation azeotrope with $CH_2Cl_2$.

EXAMPLE 8

Synthesis of 8-CNVE

EVE (1698 g, 3.9 mol) was cooled to −15° C. in a 5-liter glass pot. Anhydrous ammonia (76.4 g, 4.49 mol) was bubbled slowly through the EVE while controlling the temperature in the range of −15° to −5° C. After additon of ammonia was complete, the reaction mixture was stirred for 1 hr and allowed to warm up to 10°–15° C. Vacuum was then applied to remove excess ammonia and the methanol formed, leaving crude fluoro-amide (AVE) in the pot. DMF (1500 mL) was added to the crude AVE, and the solution was stirred and cooled to −15° C. Pyridine (354 g, 4.49 mol) was added to the solution, followed by slow addition of trifluoroacetic anhydride (TFAA, 943 g, 4.49 mol). Reaction temperature was maintained in the range of from −15° C. to −5° C. during the addition of TFAA. After TFAA addition was complete, the reaction mixture was stirred for 1 hr while allowing the mixture to warm up to room temperature. Cold water (0°–2° C., 500 mL) was added to the mixture with stirring during 10 min. When agitation was stopped, the mixture of wash water and DMF solvent separated as an upper layer, and fluoro-nitrile (8-CNVE) separated as an insoluble lower layer which was removed and distilled at atmospheric pressure to obtain 1138 g of product boiling in the range 101°–103° C. GC analysis of this distillate showed it to be 98.5% pure 8-CNVE. Yield to 8-CNVE from EVE was 75% (molar basis).

We claim:

1. In the process for reacting fluoro-ester of the formula $CF_2$=CF—$R_f$—COOR, wherein $R_f$ is perfluoroalkyl or perfluoroalkoxy containing 2–20 carbon atoms and R is alkyl having 1–6 carbon atoms, with ammonia or aqueous ammonium hydroxide to form fluoro-amide of the formula $CF_2$=CF—$R_f$—$CONH_2$, the improvement comprising carrying out said reaction in the absence of solvent, in oxygen-free solvent, or in solvent containing ether oxygen bonded to perfluoroalkyl.

2. The process of claim 1, wherein said alkyl is methyl or ethyl.

3. The process of claim 1, wherein said reaction is carried out in the absence of solvent or in oxygen-free solvent.

4. The process of claim 1, wherein said $R_f$ is –[$OCF_2CF(CF_3)$]$_n OCF_2CF_2$— and n=1–5.

5. The process of claim 4, wherein n=1.

6. The process of claim 1, further comprising reacting said fluoro-amide with dehydrating agent in polar solvent having the formula R—(CO)—NR'R", wherein R is H or alkyl having 1–6 carbon atoms, and R' and R" are independently alkyl having 1–6 carbon atoms, to form fluoro-nitrile of the formula $CF_2$=CF—$R_f$—CN, wherein $R_f$ has the same meaning as set forth in claim 1.

7. The process of claim 6, wherein R is H, and R' and R" are methyl or ethyl.

8. The process of claim 6, wherein R, R' and R" are methyl.

9. The process of claim 6, wherein said dehydrating agent is pyridine and trifluoroacetic anhydride.

10. The process of claim 6, wherein said fluoro-amide is crude fluoro-amide that is not purified.

11. In the process for reacting fluoro-amide of the formula $CF_2$=CF—$R_f$—$CONH_2$, wherein $R_f$ is perfluoroalkyl or perfluoroalkoxy containing 2–20 carbon atoms and R is alkyl having 1–6 carbon atoms, with pyridine and trifluoroacetic anhydride to form fluoro-nitrile of the formula $CF_2$=CF—$R_f$—CN, the improvement comprising carrying out the reaction in polar solvent having the formula R—(CO)—NR'R", wherein R is H or alkyl having 1–6 carbon atoms, and R' and R" are independently alkyl having 1–6 carbon atoms, to form said fluoro-nitrile.

12. The process of claim 11, wherein said $R_f$ is —[$OCF_2CF(CF_3)$]$_n OCF_2CF_2$— and n=1–5.

13. The process of claim 12, wherein n=1.

14. The process of claim 11, wherein R is H, and R' and R" are methyl or ethyl.

15. The process of claim 11, wherein R, R' and R" are methyl.

* * * * *